(12) United States Patent
Mayer et al.

(10) Patent No.: US 9,772,317 B2
(45) Date of Patent: Sep. 26, 2017

(54) METHOD FOR OPERATING A PORTABLE ELECTRONIC DEVICE

(75) Inventors: Felix Mayer, Stäfa (CH); Lukas Bürgi, Zürich (CH); Dominic Böni, Dielsdorf (CH)

(73) Assignee: Sensirion AG, Stafa (CH)

( * ) Notice: Subject to any disclaimer, the term of this patent is extended or adjusted under 35 U.S.C. 154(b) by 1004 days.

(21) Appl. No.: 13/558,436

(22) Filed: Jul. 26, 2012

(65) Prior Publication Data
US 2014/0032153 A1 Jan. 30, 2014

(51) Int. Cl.
*G01N 33/00* (2006.01)
(52) U.S. Cl.
CPC ................. *G01N 33/0006* (2013.01)
(58) Field of Classification Search
CPC ................. G01N 33/00; G06F 17/18
See application file for complete search history.

(56) References Cited

U.S. PATENT DOCUMENTS

| | | | |
|---|---|---|---|
| 4,025,412 A | 5/1977 | LaConti | |
| 4,351,181 A | 9/1982 | Currans | |
| 4,526,028 A | 7/1985 | Hubner | |
| 4,784,721 A | 11/1988 | Holmen et al. | |
| 4,809,810 A | 3/1989 | Elfman et al. | |
| 4,899,085 A | 2/1990 | Kimura et al. | |
| 5,345,213 A | 9/1994 | Semancik et al. | |
| 5,406,109 A | 4/1995 | Whitney | |
| 5,705,745 A | 1/1998 | Treutler et al. | |
| 5,792,938 A | 8/1998 | Gokhfeld | |
| 5,832,411 A | 11/1998 | Schatzmann et al. | |
| 5,873,990 A * | 2/1999 | Wojciechowski | G01N 33/48714 204/406 |
| 5,907,765 A | 5/1999 | Lescouzeres et al. | |
| 5,963,782 A | 10/1999 | Webb | |
| 6,231,516 B1 | 5/2001 | Keilman et al. | |
| 6,600,997 B2 * | 7/2003 | Deweese | G01N 33/48785 702/22 |
| 6,690,569 B1 | 2/2004 | Mayer et al. | |
| 6,697,645 B1 | 2/2004 | MacFarlane | |
| 6,703,241 B1 | 3/2004 | Sunshine et al. | |
| 6,858,182 B1 | 2/2005 | Ito et al. | |
| 7,061,061 B2 | 6/2006 | Goodman et al. | |

(Continued)

FOREIGN PATENT DOCUMENTS

| | | |
|---|---|---|
| CN | 1301342 | 6/2001 |
| CN | 1453584 | 11/2003 |

(Continued)

OTHER PUBLICATIONS

Markus Fryder et al., "A Calibration Technique for an Electronic Nose", vol. 1, Jun. 25, 1995, pp. 683-686.

(Continued)

*Primary Examiner* — Regis Betsch
(74) *Attorney, Agent, or Firm* — Cooper & Dunham LLP

(57) ABSTRACT

In a method for operating a portable electronic device comprising a chemical sensor, at least one reference reading is taken by the chemical sensor at least one predetermined point in time. At least one compensation value is determined based on at least one reference value wherein each reference value is derived from a result of a corresponding reference reading. A result of an operational reading of the chemical sensor is modified by the at least one compensation value.

8 Claims, 4 Drawing Sheets

(56) References Cited

U.S. PATENT DOCUMENTS

| | | |
|---|---|---|
| 7,104,110 B2 | 9/2006 | Oishi et al. |
| 7,911,010 B2 | 3/2011 | Stetter |
| 7,991,571 B2 | 8/2011 | Laraia et al. |
| 2002/0178789 A1 | 12/2002 | Sunshine et al. |
| 2003/0172717 A1 | 9/2003 | Kita et al. |
| 2005/0053523 A1 | 3/2005 | Brooke |
| 2005/0160789 A1 | 7/2005 | Freyer et al. |
| 2006/0130557 A1* | 6/2006 | Leddy .................. G01N 33/497 73/23.3 |
| 2007/0063853 A1 | 3/2007 | Derrick et al. |
| 2007/0241261 A1 | 10/2007 | Wendt |
| 2008/0052010 A1 | 2/2008 | Lee et al. |
| 2008/0128277 A1 | 6/2008 | Fukuda |
| 2008/0156075 A1 | 7/2008 | Cunningham |
| 2009/0126460 A1 | 5/2009 | Gardner et al. |
| 2009/0146826 A1 | 6/2009 | Gofman et al. |
| 2009/0212847 A1* | 8/2009 | Schultz ................. G01F 1/6965 327/513 |
| 2009/0325639 A1 | 12/2009 | Koehn |
| 2010/0045300 A1 | 2/2010 | Brothier et al. |
| 2010/0060465 A1 | 3/2010 | Stetter |
| 2010/0137732 A1 | 6/2010 | Haveri |
| 2010/0300443 A1 | 12/2010 | Becker et al. |
| 2011/0181421 A1 | 7/2011 | Nabata et al. |
| 2011/0206378 A1 | 8/2011 | Bolling et al. |
| 2011/0307208 A1 | 12/2011 | Graf et al. |
| 2012/0050038 A1 | 3/2012 | Stetter |
| 2012/0105084 A1 | 5/2012 | Kittleson |
| 2012/0226117 A1* | 9/2012 | Lamego ............ A61B 5/14532 600/316 |
| 2013/0192338 A1 | 8/2013 | Mayer et al. |
| 2013/0244336 A1 | 9/2013 | Mayer et al. |
| 2013/0249499 A1 | 9/2013 | Graf et al. |
| 2013/0282321 A1 | 10/2013 | Son et al. |
| 2013/0332024 A1* | 12/2013 | Garrett ................... G07C 5/008 701/29.4 |
| 2013/0344609 A1 | 12/2013 | Mayer et al. |

FOREIGN PATENT DOCUMENTS

| | | | |
|---|---|---|---|
| CN | 1825120 | 8/2006 | |
| CN | 101000357 | 7/2007 | |
| CN | 200994151 | 12/2007 | |
| CN | 101141341 | 3/2008 | |
| CN | 101470121 | 7/2009 | |
| CN | 201364320 | 12/2009 | |
| CN | 201733362 | 2/2011 | |
| CN | 102109487 | 6/2011 | |
| CN | 102192927 | 9/2011 | |
| DE | 102010027690 A1 * | 1/2012 | ............... C25B 1/04 |
| EP | 1236038 | 9/2000 | |
| EP | 1092962 | 4/2001 | |
| EP | 2392898 | 12/2011 | |
| EP | 2508881 | 10/2012 | |
| EP | 2620768 | 7/2013 | |
| EP | 2639582 | 9/2013 | |
| EP | 2642289 | 9/2013 | |
| GB | 2097130 | 10/1982 | |
| JP | 5622944 | 3/1981 | |
| JP | 2007135008 | 5/2007 | |
| JP | 2007142835 | 6/2007 | |
| JP | 2010187126 | 8/2010 | |
| JP | 2010237130 | 10/2010 | |
| JP | 2011169830 | 9/2011 | |
| KR | 100690638 | 2/2007 | |
| NO | 2011068976 | 6/2011 | |
| WO | 9222813 | 12/1992 | |
| WO | 03043356 | 5/2003 | |
| WO | 2011058224 | 5/2011 | |

OTHER PUBLICATIONS

European Search Report No. 13003312.9, dated Nov. 18, 2013.
Albrecht Schmidt et al., "How to Build Smart Appliances,?" IEEE Personal Communications, Aug. 2001, 66-71.
Nicolas D. Lane et al., "A Survey of Mobile Phone Sensing," IEEE Communications Magazine, Sep. 2010, 140-150.
"Embedded Sensors in Mobiles to Monitor Asthma", Digital Opportunity Channel, Nov. 24, 2009.
J. Puigcorbe et al., "High Temperature Degradation of Pt/Ti Electrodes in Micro-Hotplate Gas Sensors," J. Micromech, Microeng, 13, 2003, 119-124.
Isolde Simon et al., "Micromachined Metal Oxide Gas Sensors: Opportunities to Improve Sensor Performance," Sensors and Acuators B 73 (2001), 1-26.
Martin Heule, et al., "Minaturised Arrays of Tin Oxide Gas Sensors on Single Microhotplate Substrates Fabricated by Micromolding in Capillaries", Sensors and Actuators B 93 (2003), 100-106.
A. Hierlemann, "CMOS-based Chemical Sensors", Advanced Micro and Nanosystems, vol. 2, CMOS-MEMS, 335-390.
A. Loufti et al., "Odor Recognition for Intelligent Systems," IEEE Computer Society, Jan./Feb. 2008, 41-48.
A. Friedberger et al., "Micromechanical Fabrication of Robust Low-Power Metal Oxide Gas Sensors", Sensors and Acuators B 93 (2003), 345-349.
Chinese Search Report No. 2013100822711, dated Mar. 15, 2012.
European Search Report No. 13002701.4, dated Dec. 2, 2013.
Mane et al., "Explosive Detection with Mobile Telephony an Attempt Towards a Safe Ambience", Proceedings of 2011 International Conference on Signal Processing, Communication, Computing and Networking Technologies (ICSCCN 2011) pp. 187-191.
Chinese Examination Report for Application No. 201310317733.3, dated Jan. 16, 2017.

\* cited by examiner

METHOD FOR OPERATING A PORTABLE ELECTRONIC DEVICE

BACKGROUND OF THE INVENTION

The present invention relates to methods for operating a portable electronic device and to portable electronic devices.

Today's smart phones or tablet computers contain a couple of sensors such as, for example, a gyroscope or an acceleration sensor used for detecting an orientation of the device display for having the content to be displayed adapted to such orientation.

In general, chemical sensors are known for detecting an analyte in a gas or a fluid. In particular, metal-oxide sensors are chemical sensors known to be operated at elevated temperatures of a few hundred degrees Celsius. In order to achieve these temperatures in a sensitive layer of the chemical sensor a heater thermally coupled to the sensitive layer may be heated prior to and/or during taking a sensor reading. However, such metal-oxide sensors may suffer from drift even when the sensor is not operated and even in the absence of any chemical stimulus to the sensor. Drift may be understood as a variation in the sensor signal over time under identical environmental conditions. Drift may impact a transfer function of the sensor in form of an offset drift representing an additive component to the sensor signal, and/or in form of a sensitivity drift affecting an incremental gradient of the transfer function. Any drift in turn may impact the accuracy of the sensor signal.

Therefore it is desired to provide methods for operating a portable electronic device and to provide portable electronic devices comprising a chemical sensor in which an impact of a drift of the chemical sensor on an output of the chemical sensor may be reduced.

SUMMARY OF THE INVENTION

According to a first aspect of the present invention, a method is provided for operating a portable electronic device comprising a chemical sensor. At least one reference reading is taken by the chemical sensor at least one predetermined point in time. At least one compensation value is determined based on at least one reference value wherein each reference value is derived from a result of a corresponding reference reading. A result of an operational reading of the chemical sensor is modified by the at least one compensation value.

Preferred embodiments of the first aspect of the present invention may include one or more of the following features:

reference readings are taken by the chemical sensor at predetermined points in time, a prediction model is determined based on the reference values of the corresponding reference readings, and the at least one compensation value is derived from the prediction model;

the prediction model is a linear prediction model and is determined based on the reference values by means of linear regression, and the at least one compensation value is based on an offset value and a slope value of the linear prediction model;

a deviating reference value out of the reference values is excluded from contributing to determining the prediction model if said deviating reference value deviates for more than a threshold from a value provided by a prediction model determined without a contribution of the deviating reference value;

a single reference reading is taken at each predetermined point in time, and a single reference value is assigned to each single reference reading wherein said single reference value is derived from a result of said single reference reading;

two reference readings are taken at each predetermined point in time, an interval between taking said two reference readings is less than one hour, a difference between two reference values corresponding to said two reference readings is determined, and said two reference values are excluded from contributing to the prediction model if the difference exceeds a threshold;

the chemical sensor comprises multiple sensor cells, in a reference reading at a predetermined point in time the sensor cells of the chemical sensor are read, at least one compensation value is determined per sensor cell subject to the at least one reference value corresponding to said concerned sensor cell, a result of an operational reading of said concerned sensor cell is modified by the at least one compensation value determined for said concerned sensor cell;

a distance is determined between a reference vector containing the reference values of the sensor cells the reference reading is applied to and a vector of values provided by prediction models with one prediction model per sensor cell, wherein the prediction models are determined without a contribution of the reference values of said reference vector, and wherein the reference values of said reference vector are excluded from contributing to determining the prediction models for the sensor cells if said distance exceeds a threshold;

at said at least one predetermined point in time a reading is taken from at least one plausibility sensor for allowing to verify a reading of the chemical sensor, and the reference value corresponding to the result of the reference reading of the chemical sensor at the same point in time is excluded from a contribution to the prediction model subject to the result of the at least one reading taken from the at least one plausibility sensor;

the at least one plausibility sensor includes one or more of a temperature sensor and a humidity sensor and/or includes one or more sensor cells of the chemical sensor;

the at least one predetermined point in time is determined such that a predictable chemical condition of an environment of the portable electronic device is expected at such at least one predetermined point in time;

said at least one predetermined point in time is selected between 2 am and 5 am;

said predetermined points in time are defined at a specific time of day per one of days, multiple of days, weeks, multiple of weeks, months, and multiple of months;

the at least one predetermined point in time is determined by a trigger activatable by a user of the portable electronic device.

According to another aspect of the present invention, a computer program medium is provided comprising computer program code means for implementing steps of a method according to any one of the previous embodiments when executed on a processing unit.

According to a further aspect of the present invention, a portable electronic device is provided comprising a chemical sensor for detecting one or more analytes in an environment of the chemical sensor, and a control unit for modifying a chemical sensor reading by a compensation value determined subject to at least one reference value derived from a result of at least one reference reading taken by the chemical sensor at least one predetermined point in time.

Preferred embodiments of this aspect of the present invention may include one or more of the following features:

an interface for transmitting data to and receiving data from a remote determination unit, the control unit being adapted to transmit the at least one reference value to the remote determination unit via the interface, and the control unit being adapted to receive the at least one compensation value from the determination unit via the interface;

the control unit comprising a determination unit for determining the at least one compensation value subject to the at least one reference value;

the portable electronic device being one of a mobile phone, a handheld computer, an electronic reader, a tablet computer, a game controller, a pointing device, a photo or a video camera, and a computer peripheral.

According to a further aspect of the present invention, a system is provided comprising a portable electronic device according any one of the previous embodiments, and a remote determination unit for determining the at least one compensation value subject to the at least one reference value received via the interface and for transmitting the at least one compensation value via the interface to the portable electronic device.

According to another aspect of the present invention a portable electronic device is provided comprising a chemical sensor for detecting one or more analytes in an environment of the chemical sensor, and a control unit for modifying a chemical sensor reading by a compensation value determined subject to one or more of operational data of the portable electronic device, values measured by a sensor of the portable electronic device, data from a remote portable electronic device with a chemical sensor, and data from a remote determination unit for determining compensation values.

Preferred embodiments of the further aspect of the present invention may include one or more of the following features:

an interface for transmitting data to and receiving data from a remote determination unit, the control unit being adapted to transmit the one or more of the operational data of the portable electronic device and the values measured by the sensor of the portable electronic device to the remote determination unit via the interface;

the operational data of the portable electronic device containing one or more of: heating related data in case the chemical sensor comprises a heater; operating hours of the chemical sensor; a sensor identifier.

the sensor of the portable electronic device comprising one or more of a humidity sensor and a temperature sensor, and the values measured by the sensor of the portable electronic device comprising humidity values measured by the humidity sensor and/or temperature values measured by the temperature sensor respectively.

According to a further aspect of the present invention, a system is provided comprising a portable electronic device according to any one of the previous embodiments, and a remote determination unit for receiving and storing the one or more of the operational data of the portable electronic device and the values of the sensor of the portable electronic device, for determining the at least one compensation value subject the to one or more of the data representing an operational parameter of a remote portable electronic device with a chemical sensor, values of a sensor of the remote portable electronic device, and other data available to the remote determination unit, and for transmitting the at least one compensation value via the interface to the portable electronic device.

According to another aspect of the present invention, a method is provided for operating a portable electronic device comprising a chemical sensor, the method comprising the portable electronic device transmitting one or more of operational data of the portable electronic device and values of a sensor of the portable electronic device to a remote determination unit, receiving at least one compensation value from the determination unit, taking a chemical sensor reading, and modifying the chemical sensor reading by the at least one compensation value.

In a preferred embodiment, the remote determination unit determines the at least one compensation value as a result of a prediction model determined by the one or more of the operational data of the portable electronic device and the values of the sensor of the portable electronic device. In another preferred embodiment, the remote determination unit may determine the at least one compensation value dependent on one or more of data representing an operational parameter of a remote portable electronic device with a chemical sensor, values of a sensor of the remote portable electronic device, and other data available to the remote determination unit.

According to another aspect of the present invention, a computer program medium is provided comprising computer program code means for implementing steps of a method according any one of the previous embodiments when executed on a processing unit.

Other advantageous embodiments are listed in the dependent claims as well as in the description below.

The described embodiments similarly pertain to the apparati, the methods and the computer program media. Synergetic effects may arise from different combinations of the embodiments although they might not be described in detail.

BRIEF DESCRIPTION OF THE DRAWINGS

The embodiments defined above and further aspects, features and advantages of the present invention can also be derived from the examples of embodiments to be described hereinafter and are explained with reference to the drawings. In the drawings the figures illustrate in FIG. 1 a mobile phone according to an embodiment of the present invention, FIG. 2 a top view on a sensor chip according to an embodiment of the present invention, FIG. 3 a cut through an individual sensor cell of the sensor chip of FIG. 2, FIG. 4 a block diagram of a portable electronic device according to an embodiment of the present invention, FIG. 5 a flow chart representing a method for operating a portable electronic device according to an embodiment of the present invention, and FIG. 6 a diagram illustrating the building of a prediction model as used in an embodiment of the present invention.

DETAILED DESCRIPTION OF THE DRAWINGS

Figure 1:
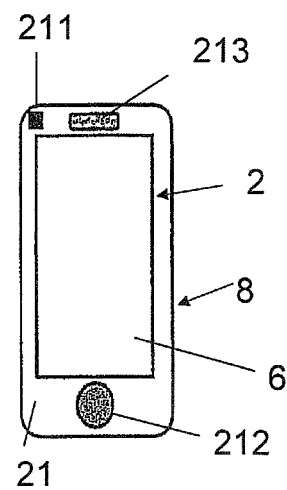

A chemical sensor may in one embodiment of the present invention comprise at least one sensor material, e.g. in form of a layer. An analyte present in an environment of the chemical sensor may interact with the chemical sensor and as such may modify an electrical property of the sensor material such as its electrical conductance. Then, the electrical property of a combination of the analyte and the sensor material may be measured and allows a conclusion as to the analyte, such as by way of comparison to a property of the sensor material measured without the presence of the analyte. An analyte may, for example, be a chemical element or a chemical compound. Specifically, the chemical sensor may be a gas sensor for detecting one or more substances in a gas, and specifically in the air surrounding the portable electronic device. Hence, in a sample application it may be of interest to identify if such air may contain analytes the chemical sensor is prone to. Specific applications may include the detection of toxic gases, the detection of ethanol in a users breath, or the detection of other substances, but also the detection and/or identification of odours.

The chemical sensor preferably is arranged inside a housing of the portable electronic device. An opening may be provided in the housing for exposing the chemical sensor to a fluid to be analyzed.

Hence, any portable electronic device such as a mobile phone, and in particular a smart phone, a handheld computer, an electronic reader, a tablet computer, a game controller, a pointing device, a photo or a video camera, or a computer peripheral—which listing is not limited—may in addition to its original function provide chemical information as to its environment. The user may learn about chemical substances and compositions present in the devices surroundings, and may use, transmit or else further analyse such information. For the reason that such portable electronic device typically includes interfaces to a remote infrastructure, such information may be transmitted elsewhere and be used elsewhere. In an alternative, the user himself/herself may benefit from the information provided by the chemical sensor in that actions can be taken in response to detected analytes, including but not limited to analytes representing toxic substances. Such portable electronic device as a result may primarily be designed for computing and/or telecommunication and/or other tasks in the IT arena, and now may be enhanced by the function of providing chemical information as to its environment.

For the reason that many chemical sensors operate as introduced above, preparation may need to be taken prior to a sensor reading as, for example, the sensor material may require to be heated prior to having its conductance changed upon an interaction with the analyte. Taking a reading by the chemical sensor in this context may require, for example, an upfront heating while conductivity results may be measured/gained/taken during the sensor material being sufficiently heated.

The chemical sensor may be affected by drift. i.e. the sensor signal as output of the sensor may show one or both of ab offset drift and a sensitivity drift. While the offset drift may represent an output of non-zero at zero input, i.e. for example in the absence of an analyte the chemical sensor is sensitive to, the sensitivity drift may represent a drift of an incremental gradient of a transfer function of the chemical sensor which transfer function between sensor input and sensor output. For determining a corrective to an undesired drift in the chemical sensor signal, at least one reference reading is taken by a chemical sensor of the portable electronic device at at least one predetermined point in time. The reference reading has a different aim than an operational reading since the reference reading is meant for determining offset compensation values which may be applied to future operational readings. In contrast, the operational reading aims at gaining information about chemical substances or analytes in the surroundings of the portable electronic device.

The reference readings are conducted at least one predetermined point in time. Such predetermined point in time preferably is a point in time when stable chemical conditions can be expected in the environment. In case of determining multiple points in time, such points in time are chosen such that across all points in time the chemical conditions in the environment are stable and identical to each other. Preferably, the points in time are periodical points in time.

In a specific example, such predetermined point in time may be for example at 4 am for the reason that a user of the portable electronic device may typically have the portable electronic device deposited in some room at home for a battery recharge where it can safely be expected that the chemical exposure in such room may not be different from night to night. In particular, the predetermined points in time may be defined as a specific time of day per one of days, multiple of days, weeks, multiple of weeks, months, and multiple of months. Hence, for example, the predetermined points in time may be determined as 4 am every 24 hours. The predetermined point in time may be defined in a different way, however, it shall in some way either be predetermined by specific dates and hours, or by some means of algorithm, or by support of measurements which indicate at which point in time it would be best to conduct a reference measurement by taking reference readings. In a specific embodiment, a user of the portable electronic device may either be enabled to adjust the predetermined point in time, or may input the predetermined point in time on his/her own. And in another embodiment, a user may immediately trigger for a reference reading in case he/she believes to have suitable environment conditions.

Given that the one or more predetermined points in time should preferably denote points in time with a predictable chemical condition of the environment of the portable electronic device, the reference measurements/readings taken by the chemical sensor should ideally provide the same results across many reference readings over time in case the chemical sensor is an ideal sensor. However, as introduced above the chemical sensor may suffer from an offset and/or sensitivity drift one or both of which drifts may preferably be determined by means of the results of the reference readings. Given that the chemical sensor undergoes drift the reference measurements/readings taken by the chemical sensor at the predetermined points in time will provide varying results, e.g. varying in amplitude which variation is owed to the drift phenomenons.

A result of a reference reading may preferably be referred to as reference value which may be equal to the value supplied from the chemical sensor, i.e. a raw value, or which may be a value determined/calculated from the raw value. Hence, in an offset drift situation, the reference value may change from reference reading to reference reading. Any such course of reference values may be captured and possibly be stored. From these reference values, a prediction model may be determined by some technique. The prediction model may allow for predicting future drifts which may be calculated and be applied to future operational readings of the chemical sensor. There may be determined a prediction model for both, offset and sensitivity drift, in case it is aimed at determining compensation values for both the offset and the sensitivity drift. Hence, future drift values may be extrapolated from the known drift values. Any technique performing such prediction model may be applied to the reference values representing the drift values of the past. Summarizing, at least one compensation value is determined based on at least one reference value which is based, and possibly is identical to a result of one or more reference readings. A result of a future operational chemical sensor reading may then be modified by the at least one compensation value, for example, the compensation value may be added to the chemical sensor value read or be multiplied by it in case the compensation value represents a correction of the offset drift.

For determining the prediction model, a model technique referred to as linear regression may be applied which results in a liner curve determined based on the individual reference values. Parameters which characterize such curve—i.e the prediction model—may, for example, be a prediction model offset value at t=0, and a prediction model slope value—in short slope—of the linear curve. These two parameters may be taken as compensation value changing over time as these values allow for predicting future offset drift values at future time t. It can be determined which offset drift value can be reasonably expected at future time t from the linear curve determined by the slope and the prediction model offset value at t=0.

Summarizing, the present idea may compensate for drifts, and specifically for drifts in the signal of a chemical sensor which improves the measurement quality.

The method as introduced may in one embodiment allow for only a single reference measurement at a predetermined point in time. A single measurement may in some cases be sufficient and its associated reference value may directly be taken as compensation value. In another embodiment, reference readings may be taken at multiple predetermined points in time, e.g. periodically, preferably at the same time of day each day/week or month, for example. A single measurement may be conducted at each point in time such that at each point in time a reference value is generated which is identical or derived from the result of the reference measurement. Such reference values may preferably be stored in a non-volatile memory of the portable electronic device or at a remote location.

At some point in time, e.g. after having taken a predefined number of reference readings, the at least one compensation value may be determined based on the reference values corresponding to the reference reading results. The one or more compensation values may include one or more values to be applied to future operational reading results for compensating for drift components. Such compensation values may, for example, be values added, multiplied, subtracted or divided with/by the measured/read values in a future operational reading.

In another approach, the reference values are used for determining a curve as a prediction model. Such curve can be determined by the present and past reference values, and may be mathematically and or selectively be described and/or extrapolated for the future. Such prediction model is determined based on the reference values collected. The prediction model specifically exhibits the offset or sensitivity drift respectively over time. Preferably a linear prediction model may be used for describing the drift over time, and preferably a method known as linear regression is used for obtaining the linear prediction model from the reference values.

In another variant, a non linear prediction model may be applied for describing the course of the drift over time. Other determination methods such as exponential term drift may be applied for determining the prediction model.

In gathering reference values there may be some values that may be considered as runaway values, i.e. these reference values may be outside a statistical distribution of reference values or represent a very low likelihood of appearance. This may be the case, when for example the environmental conditions at the predetermined point in time have fundamentally changed from the ones expected. For example, the user was out in a pub at the predetermined time of day instead of having his mobile phone being deposited in his apartment for recharge. Such runaway values may possibly falsify the prediction model when being taken into consideration. This is why in a preferred embodiment, the prediction model is determined from reference values excluding such one or more runaway reference values. In case a value deviates from the value provided by a prediction model generated without a contribution of the runaway value by more than a threshold such runaway value may be excluded from contributing to building the prediction model. However, in case the value is below the threshold, the value may be allowed to contribute to the prediction model.

In a different embodiment, instead of taking a single sensor reading per predefined point in time, two consecutive sensor readings may be taken per predefined point in time wherein an interval between these two readings is rather short in comparison to an interval between two consecutive predetermined points in time. The interval between the subject two reference readings preferably is less than one hour, and in a very much preferred embodiment less than twenty minutes. A difference between reference values corresponding to these two reference readings is determined. In case the difference of the first and the second reference value is equal to or within the threshold, a mean value of the two reference values may be determined and used in contributing to the prediction model. Instead of the mean value, one of the lower and the higher reference value may be used. In case the difference exceeds a threshold, both reference values may not be allowed to contribute to the building of the prediction model. Alternatively, a third measurement can be taken with a defined interval between the second reference reading and the third reference reading. If the difference between third and second corresponding reference values is within a threshold, then the mean of the second and the third reference value may be taken as a reference value contributing to the prediction model.

In another embodiment, the chemical sensor may comprise multiple sensor cells which sensor cells build for a sensor array. Such chemical sensor may typically be used for detecting different analytes wherein each cell may primarily be sensitive to a specific analyte. In a reference reading at a predetermined point in time, the—and preferably all—sensor cells of the chemical sensor are read, i.e. all sensor cells take a measurement such that each sensor cell provides an individual measurement result, i.e. a sensor cell reading. Hence, each measurement result is represented by a corresponding reference value such that a chemical sensor reading at a single predetermined point in time results in multiple reference values combined into a reference vector wherein the individual reference values are derived from measurement results of the individual sensor cells. A compensation value may now be assigned to each sensor cell for compensating the individual offset drift of such sensor cell. Hence, per sensor cell, reference values read at multiple different predetermined points in time may be used for building a prediction model for the offset drift of this particular sensor cell. At least one compensation value may then be derived from the prediction model for compensating any offset drift of this particular sensor cell. A result of an operative sensor cell reading may then be modified by the at least one compensation value determined for the concerned sensor cell.

When it comes to the problem of runway values in chemical sensor arrays, the treatment as introduced above may in one embodiment be applied to every single sensor cell.

However, in a different embodiment, the reference values from a common reading of all sensor cells may in combination be compared to values provided by prediction models for the sensor cells which prediction models were determined without a contribution of the reference values of the reference vector. Hence, a distance between such vectors may be determined by $$|s(t_i)-r(t_i)|$$

wherein $s(t_i)$ is a vector including values from prediction models for time $t_i$ to which prediction models the reference vector at time $t_i$ has not contributed to, and wherein $r(t_i)$ is the reference vector. The values of the reference vector $r(t_i)$ will be excluded from contributing to the various prediction models in case the distance according to the above formula exceeds a threshold.

In another embodiment, a reference reading may be taken at a predetermined point in time by the chemical sensor and by one or more sensors of the portable electronic device, also referred to plausibility sensors. A contribution of a reference value corresponding to this predetermined point in time may be made dependent from the result of the reading of the one or more plausibility sensors. The plausibility sensor allows verifying a reading of the chemical sensor at least at a plausibility level. Specifically, such plausibility sensor may be a temperature sensor or a humidity sensor. However, in a different embodiment, the plausibility sensor may also be represented by one or more individual sensor cells of the chemical sensor itself in case the chemical sensor is built as a sensor array containing multiple sensor cells.

For example, the reference value from a reference reading by the chemical sensor may be excluded from a contribution to the prediction model, if a temperature measured at the very same predetermined point in time by a temperature sensor is above value x or below value y, with, for example, x=30° and y=15°. In case the sensor is a humidity sensor the reference value from a reference reading by the chemical sensor may be excluded from a contribution to the prediction model, if a relative humidity measured at the very same predetermined point in time by a humidity sensor is above value m or below value n, with, for example, n=20% RH (relative humidity) and m=60% RH. In a third example, the chemical sensor is a sensor array with multiple sensor cells. In such embodiment, a reference vector containing reference values from a reading by the chemical sensor at a predetermined point in time is excluded from a contribution to the respective prediction models in case the reference value corresponding to one or more dedicated sensor cells exceeds a threshold, for example.

The determination of the compensation value/s including a possible determination of one or more prediction models for the offset drift and/or the sensitivity drift may be executed either on the portable electronic device itself, or at a remote location. In the first alternative, the determination unit for doing so preferably is part of the control unit.

In the second alternative, the portable electronic device preferably comprises an interface for transmitting data to a remote determination unit, and the control unit of the portable electronic device is adapted to transmit the at least one reference value to the remote determination unit via this interface. On the other hand the control unit of the portable electronic device is adapted to receive the at least one compensation value from the determination unit via the interface such that the compensation value can be applied to future operational chemical sensor readings for compensating for an offset drift.

For the second alternative, a system is provided comprising a portable electronic device according to the above embodiment, and a remote determination unit for determining the at least one compensation value subject to the at least one reference value received via an interface between the portable electronic device and the determination unit and for transmitting the at least one compensation value via the interface to the portable electronic device. The remote determination unit preferably is a computing unit of a server connected to the internet, or is a server in a cloud.

The chemical sensor may, for example, comprise a sensitive layer and a heater for heating the sensitive layer. The control unit of the portable electronic device may activate the heater prior to and/or during taking a measurement. Especially, such chemical sensors to be operated at elevated temperatures may suffer from an offset drift when the sensor is not operated, i.e. especially when the heater is not activated for a long time, e.g. for the reason of adsorption of water into the sensitive layer. However, such drift may be reversible and an existing drift can be compensated by activating the heater and by heating the sensitive layer for a sufficient period of time. However, in case such reconditioning heating may not have been executed for a while or cannot fully be applied in view of a sudden operational measurement request the present idea of a signal compensation supports an offset drift reduced measurement.

According to a different embodiment, it may be beneficial for determining the at least one compensation value based on one or more operational data of the portable electronic device, such as based on heating data in case the chemical sensor includes a heater as introduced above, and specifically may be based on a cumulative time the heater was activated or deactivated in a given period in time, for example, for the entire lifetime of the chemical sensor, instead or in addition to the determination of the at least one compensation value from the reference value/s of the chemical sensor. For example, the less the heater was activated over a certain period in time, the more likely a drift has occurred such that the compensation value preferably is dimensioned to compensate for a larger drift. Specifically, the compensation value may grow with enduring non-heating periods. In another embodiment, the compensation value may be determined subject to the period in time since the last heating of the heater. Specifically, the compensation value may grow with an enduring non-heating period since then.

In another embodiment, instead or in addition to the operational data, the at least one compensation value may be determined based on sensor readings, also denoted as values, from a sensor of the portable electronic device either different to the chemical sensor, or including one or more sensor cells of the chemical sensor comprising multiple sensor array cells. A sensor of the portable electronic device may, in one example, be a humidity sensor, or may, in another example, be a temperature sensor. In case the sensor is embodied as a humidity sensor, humidity values stored over a period in time may allow for a determination of the at least one compensation value in view of humidity impacting the drift in chemical sensors as laid out above. The compensation value may then depend on the previous and or present humidity measurements by a suitable function. For example, the more humidity was sensed over a period in time, which condition may be represented by an integration of humidity sensor values over the period in time and a comparison of the integrated humidity values to a threshold, the more likely the chemical sensor may show a substantial drift which in turn requires a compensation value dimensioned to compensate for such substantial drift. In evaluating the humidity over time of the past, more recent humidity values may be weighted more than more previous humidity values. Specifically, the compensation value may grow with a growing accumulated humidity. Hence, the sensor other than the chemical sensor may be any sensor that qualifies in allowing at least for an assessment of a drift of the chemical sensor. A cell of the chemical sensor itself may support determining the compensation signal. For example, in a sensor array comprising multiple sensor cells for detecting different analytes a sensor cell detecting CO may provide information as to drift effects given that some sensing layers may show a CO dependency in their drift.

Again, the determination of the compensation value may be implemented as part of the control unit in the portable electronic device. In another variant, the portable electronic device is adapted to transmit the operational data or the values measured by the sensor different to the chemical sensor to a remote determination unit via an interface of the portable electronic device. Preferably, the interface is a wireless interface, and the remote determination unit is represented by one or more servers connected to the internet providing a service of storing the received data and values and calculating the at least one compensation value therefrom. Hence, storing the relevant data and/or sensor values as well as the determination of the compensation value may be performed in the "cloud".

In another embodiment, the compensation value for the present portable electronic device may be dependent in addition or exclusively on one or more data representing an operational parameter of a remote portable electronic device with a chemical sensor, and/or values of a sensor of the remote portable electronic device. In such embodiment, other portable electronic devices submit data relevant to determining a compensation value either directly to the present portable electronic device or to a remote determination unit where the compensation value is determined and sent to the present portable electronic device. In such embodiment, it is assumed that sensors of a common lot, for example, show a common drift tendency that may be verified at any sensor of the lot. Hence, at least with respect to a lot-related drift component a determined compensation value may be transmitted to any portable electronic device of the lot such that in a specific embodiment, the chemical sensor of a portable electronic device may be compensated by means of measurement or data stemming completely from other portable electronic devices of the same lot. Hence, it may be beneficial to submit a sensor identifier to the remote determination unit enabling the determination unit to address chemical sensors of the same lot. In another embodiment, the compensation data is provided by the remote determination unit itself, e.g. by the manufacturer of the chemical sensors who runs the determination unit. Here, knowledge of the manufacturing process may help in determining lot-specific compensation values that may be transmitted to the subject portable electronic devices of the same lot, for example.

With respect to the chemical sensor itself, there may be one or more preferred embodiments applied: The chemical sensor preferably comprises a layer that is sensitive to one or more analytes a presence of which shall be detected in a gas supplied to the chemical sensor. There may be a single sensitive layer made from a uniform material for interacting with the one or more analytes. Or there may be multiple sensitive layers made from different materials, for example, for interacting with different analytes. The chemical sensor performs a detection of chemical substances or compounds which are also denoted as analytes contained in a gas, or possibly in a fluid. Analytes may be, for example, $CO_2$, $NO_X$, ethanol, CO, ozone, ammonia, formaldehyde, or xylene without limitation. Specifically, the sensitive layer may contain a metal-oxide material, and in particular a semiconducting metal oxide material. Such metal oxide material may include one or more of tin oxide, zinc oxide, titanium oxide, tungsten oxide, indium oxide and gallium oxide. Such metal oxides may be used for the detection of analytes such as VOCs, carbon monoxide, nitrogen dioxide, methane, ammonia or hydrogen sulphide. Metal-oxide sensors are based on the concept that gaseous analytes interact with the metal oxide layer at elevated temperatures of the sensitive layer in the range of more than 100° Celsius, and specifically between 250° C. and 350° Celsius. As a result of the catalytic reaction, the conductivity of the sensitive layer may change which change can be measured. Hence, such chemical sensors are also denoted as high temperature chemoresistors for the reason that a chemical property of the analyte is converted into an electrical resistance at high temperatures of the sensitive layer.

In case the chemical sensor is sensitive of multiple different analytes the chemical sensor may be embodied as a sensor array. In such sensor array, each sensor cell may provide a sensor material, e.g. in form of a layer which is also denoted as sensitive layer, an analyte may interact with. In response to the interaction an electrical property of the sensor material such as its electrical conductance, may change which principle preferably is applied in metal oxide chemical sensors. In such scenario, the sensor array may comprise a single heater for all sensor cells, or may comprise multiple heaters, wherein each heater may be assigned for heating a group of sensor cells or an individual sensor cell, or the corresponding sensitive layer respectively. In case of multiple heaters, preferably all heaters are activated during reconditioning.

In another embodiment, the chemical sensor may comprise a single sensor cell, e.g. with a single layer, which however, may be sensitive to multiple different analytes under different operating conditions. For example, the sensor cell may mainly be sensitive to a first analyte x when being heated to a first temperature tx, and may mainly be sensitive to a second analyte y when being heated to a second temperature ty which is different from the first temperature tx. In this context, the chemical sensor may be understood as containing multiple virtual sensor cells characterized by the operating conditions the one real sensor cell is exposed to. In another variant, a sensor array may comprise multiple sensor cells wherein at least one of the multiple sensor cells—and in another variant preferably all of the multiple sensor cells—is designed such that such cell/s may mainly be sensitive to different analytes under different operating conditions such as under different temperatures.

Same or similar elements are referred to by the same reference numerals across all Figures.

FIG. 1 illustrates a mobile phone 8 according to an embodiment of the present invention. Apart from a standard microphone as an input device which microphone is arranged in an opening 212 of a front wall 21 of a housing 2—which microphone may also be arranged in an opening of a side wall of the mobile phone 8, a chemical sensor is arranged in another opening 211 of the front wall 21, which opening 211 is arranged in proximity to yet another opening 213 for a standard speaker of the mobile phone 8. The chemical sensor may be used for detecting the presence of a gas or an odour in an environment of the mobile phone 7.

Figure 2:
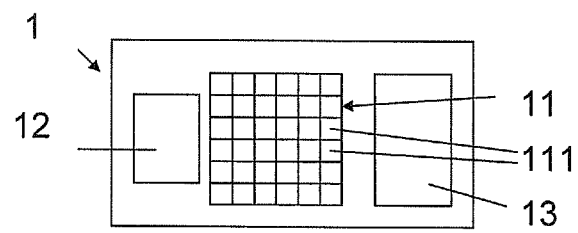

FIG. 2 illustrates a top view on a chemical sensor 1 represented by a sensor chip such as may be used, for example, in the mobile phone 8 of FIG. 1. The chemical sensor 1 comprises a chemical sensing area 11 which takes the shape of a sensor array comprising multiple sensor cells 111, in the present example, thirty six sensor cells 111. In addition a humidity and/or temperature sensitive structure 12 is arranged next to the chemical sensor array, and electronic circuitry 13 is integrated into the chemical sensor chip, too.

Figure 3:
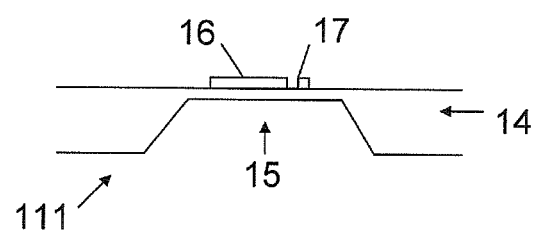

FIG. 3 illustrates a cut through a schematic individual sensor cell 111 in which a recess 15 is manufactured into a substrate 14 of the sensor chip. On top of a resulting thin membrane a sensitive layer 16 is arranged, and a heater 17, preferably a resistive heater 17, is arranged in or on top of the membrane. The membrane is also denoted as micro-hotplate for the reason that such membrane to a large extent constitutes a thermally insulating structure. Hence, any heat generation by the heater 17 affects the sensitive layer 16 as desired but does not leak into the bulk. The sensitive layer 16 preferably is made from a metal oxide material such as tin oxide. The sensitive layer 16 is heated by the heater 17 prior to taking a sensor reading, and preferably during taking a sensor reading for elevating a temperature of the sensitive layer 16 to a temperature sufficient for having a catalytic reaction between the analyte/s and the sensitive layer 16 to take place at a sufficient rate and as a result, for example, for having an electrical conductivity of the sensitive layer 16 modified. Such operating temperatures may vary subject to the material used from 100° degrees Celsius to 450° degrees Celsius. The micro-hotplate, preferably fabricated in MEMS technology, enables to achieve these temperatures in the sensing area without excessive power dissipation, since only a few 10 mW of electrical power is required for heating. While such power levels may be prohibitive for continuous mode measurements in mobile applications, single shot measurements, whereby the sensitive layer is powered up for a short time, e.g. in the order of 1 minute—and a single or a few measurement readings are taken, are possible.

Figure 4:
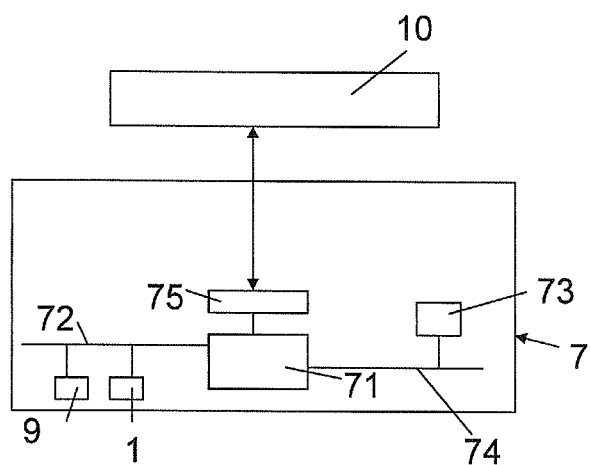

FIG. 4 shows a schematic hardware oriented block diagram of a portable electronic device 7. Here, a control unit 71 in form of a microprocessor is connected via electrical conductors 72 to multiple sensors including the chemical sensor 1, and to a microphone 9. A routine for triggering a reference reading of the chemical sensor at predetermined points in time may be executed in the control unit 71 as well as a storing of a reference value associate with the reference reading. Such actions may be initiated by the control unit 71. In addition, the control unit 71 may be adapted for determining a prediction model from the various reference values and may be responsible for determining the compensation values as well as applying these compensation values to the results of future operational readings. The routines for doing so may be stored in the memory 73 connected to the microprocessor 71 via a bus system 74. The reference values determined may be stored there, too, as may be the prediction model and/or its parameters in from of compensation values. The portable electronic device may contain a wireless interface 85 connected to the control unit 71.

In another variant, the functions that are implemented by the control unit 71 in the portable electronic device may also be outsourced to a server, a data cloud, a computing unit, or other calculating means remote from the portable electronic device. In a preferred embodiment, such external determination unit may be implemented in a data cloud representing calculation and storage capacity distributed across a network such as the Internet. Hence a determination of the prediction model and its compensation parameters may be implemented at some remote location in the cloud 10, see FIG. 4. In this embodiment, the control unit 71 of the portable electronic device transmits the reference values gained by means of the reference readings via the interface 75, which is preferably a wireless interface, to the cloud 10. Preferably, together with each reference value a time stamp and a sensor identifier is transmitted to the cloud 10. All this data is stored in the cloud 10. After having received sufficient reference values, wherein a sufficient number may be, for example, between 10 and 20—the cloud 10 may determine the compensation values based on the reference values, and may send the compensation values via the interface 75 to the portable electronic device. The same mechanism may apply when it is not values of reference readings building the basis for the determination of the compensation value but operational data of the chemical sensor, such as an accumulated heating time of a heater of the chemical sensor, or values measured by a humidity sensor of the portable electronic device, for example. Then, these data and/or values may be transmitted to the remote determination unit 10 via the interface 75 and used there for determining the compensation value, e.g. comprising an offset compensation value and a slope compensation value.

Managing the reference values and/or the operational data and/or the values from other sensors on a central server in the cloud for example opens additional options for adaptive offset and/or slope compensation. Hence, the compensation value/s may also be determined based on other information. An example of such other information is given in the following: Sensors are typically manufactured in lots. Any manufacturing specifics, impacts or exposures may in many cases apply to an entire lot of sensor devices such that the sensor devices of a common lot exhibit the same characteristic. If such lot dependent data is known to the server/cloud 10, for example, because other sensors of the same lot have reported about such characteristics, the compensation value may also be based on a lot dependent value, for example. Sensors from a common lot may be identified via the sensor identifier. Hence, if a lot dependent field behaviour could be identified for sensors of a lot and fed back to the sensors. For instance, it is known to the cloud 10 that certain lots of sensors, which have been produced from a particular batch of sensing material, show a particularly strong drift over time. The mean drift coefficient (signal change per time interval) for this lot could then be forwarded to all sensors from these lots and the drift could be compensated accordingly.

Figure 5:
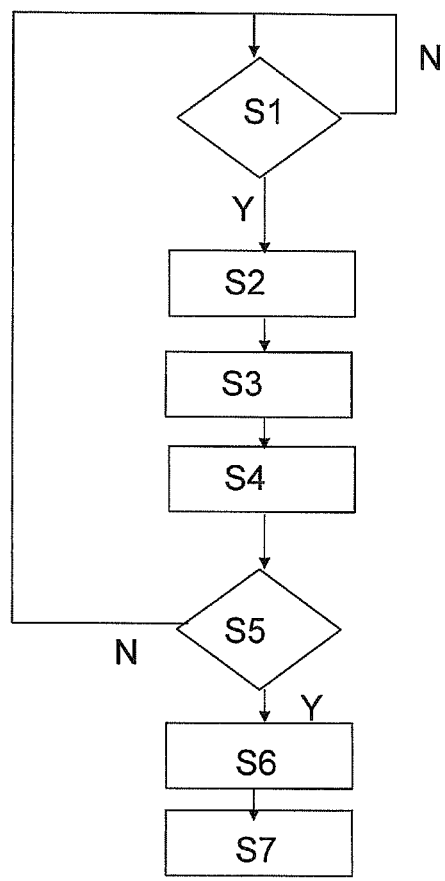

FIG. 5 illustrates a flow chart representing a method according to an embodiment of the present invention. In step S1, it is monitored if a predetermined point in time is reached. If not (N) the monitoring for the predetermined point in time continues. If yes (Y), a sensor reading is taken by the chemical sensor in step S2. This step S2 may include a prior heating of a sensitive layer of the chemical sensor or other preparation processes. In step S3, the results of the sensor reading are stored in a non-volatile memory in form of reference values together with a time stamp and possibly a sensor identifier. In step S4 a counter is increased, and in step S5 it is determined if the counter has reached a threshold. The counter in this example shall determine how many reference values are required for building a prediction model from. In case there is not a sufficient number of reference values determined yet (N) it is returned to step S1 where it is waited for the next predetermined point in time. If there is yet a sufficient number of reference values (Y) in step S5, the prediction model is determined in step S6, and the compensation values are derived from the prediction model and are stored, all in step S6. In step S7 the compensation values are applied to operational sensor readings. At this stage, an interrupt routine may make the process jump from step S7 to step S1 when a predetermined time is reached for restarting reference value readings.

Figure 6:
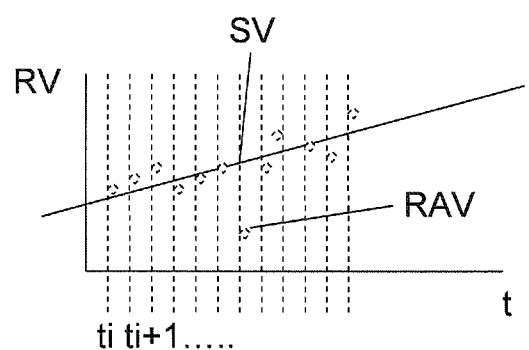

FIG. 6 illustrates an embodiment of building a prediction model from various reference values RV as measured and stored. Each ti, ti+1, . . . represents a predetermined point in time at which a reference reading is conducted by the chemical sensor. The dots in FIG. 6 represent reference values RV obtained at the various points in time. As can be seen the reference values RV are more or less nicely arranged around a linear prediction model drawn in as a straight line, except for a single reference value encircled. This reference value may be considered as runaway value RAV. Now, a prediction model is formed without any contribution of such runaway value RAV. Such prediction model may be represented by the straight line in FIG. 6. Then, a deviation of the runaway value RAV from a value SV of the prediction model at this specific point in time— which prediction model is built without the runaway value RAV—is investigated and if this deviation exceeds a threshold, the runaway value RAV may not be allowed to contribute to the prediction model.

The present portable electronic device may be used within an odour and/or gas identification system.

Generally, reference values shall belong to a common batch as long as the reference values of a common batch contribute to the same prediction model. This makes it clear, that at minimum, only the present batch of reference values needs to be stored for finally determining the prediction model once the last reference value for the present batch is received. In another embodiment, the prediction model may be determined always on the latest x reference values such that the storage may be embodied as a FIFO of length x. This concept is also known as sliding window. It is only the most recent x reference values that preferably are stored such that this embodiment saves memory space.

Preferably, any reference value is always stored together with a time stamp when the corresponding reading is taken.

While there are shown and described presently preferred embodiments of the invention, it is to be distinctly understood that the invention is not limited thereto but may be otherwise variously embodied and practised within the scope of the following claims.

The invention claimed is:
1. Portable electronic device, comprising
a chemical sensor for detecting one or more analytes in an environment of the chemical sensor, and
a control unit for modifying a chemical sensor rending by a compensation value determined subject to at least one reference value derived from a result of reference readings taken by the chemical sensor at predetermined points in time with a predictable chemical condition of the environment of the portable electronic device, which reference readings in case of an ideal chemical sensor would result in same results, for periodically recalibrating the sensor during a series of tests using the same sensor,
wherein the chemical sensor is a gas sensor for detecting one or more substances in a gas,
wherein the gas sensor is a metal-oxide sensor comprising a metal oxide layer interacting with analytes at elevated temperatures of the metal-oxide layer in a range of more than 100° C.,
wherein the metal-oxide sensor comprises a heater thermally coupled to the metal-oxide layer for heating the metal-oxide layer to the elevated temperatures,
wherein the compensation value is for compensating for a drift of the chemical sensor occurring when the heater of the chemical sensor is not activated for some time, and
wherein drift is understood as a variation in the signal of the chemical sensor over time under identical environmental conditions.

2. Portable electronic device according to claim 1, comprising an interface for transmitting data to and receiving data from a remote determination unit,
wherein the control unit is adapted to transmit the at least one reference value to the remote determination unit via the interface, and
wherein the control unit is adapted to receive the at least one compensation value from the determination unit via the interface.

3. Portable electronic device according to claim 1, wherein the control unit comprises a determination unit for determining the at least one compensation value subject to the at least one reference value.

4. Portable electronic device according to claim 1, wherein the portable electronic device is one of:
a mobile phone,
a handheld computer,
an electronic reader,
a tablet computer,
a game controller,
a pointing device,
a photo or a video camera,
a computer peripheral.

5. System, comprising
a portable electronic device according to claim 2, and
a remote determination unit for determining the at least one compensation value subject to the at least one reference value received via the interface and for transmitting the at least one compensation value via the interface to the portable electronic device.

6. Portable electronic device, comprising
a chemical sensor for detecting one or more analytes in an environment of the chemical sensor,
a control unit for modifying a chemical sensor reading by a compensation value determined subject to one or more of data representing an operational parameter of the portable electronic device, values measured by a sensor of the poi table electronic device, data from a remote portable electronic device with a chemical sensor, and data from a remote determination unit for determining compensation values,
said device comprising an interface for transmitting data to and receiving data from a remote determination unit,
wherein the control unit is adapted to transmit the one or more of data representing an operational parameter of the portable electronic device and the values measured by the sensor of the portable electronic device to the remote determination unit via the interface, and is adapted to receive the compensation value from the remote determination unit via the interface, and
wherein the data representing an operational parameter of the portable electronic device contains one or more of:
heating related data; and
operating hours of the chemical sensor,
wherein the gas sensor is a metal-oxide sensor comprising a metal oxide layer interacting with analytes at elevated temperatures of the metal-oxide layer in a range of more than 100° C., wherein the metal-oxide sensor comprises a heater thermally coupled to the metal-oxide layer for heating the metal-oxide layer to the elevated temperatures, wherein the compensation value is for compensating for a drift of the chemical sensor occurring when the heater of the chemical sensor is not activated for some time, and wherein drift is understood as a variation in the signal of the chemical sensor over time under identical environmental conditions.

7. Portable electronic device according to claim 6, wherein the sensor of the portable electronic device comprises one or more of a humidity sensor or a temperature sensor, and wherein the values measured by the sensor comprises humidity values measured by the humidity sensor and/or temperature values measured by the temperature sensor respectively.

8. System, comprising a portable electronic device according to claim 6, and a remote determination unit for receiving and storing the one or more of the data representing an operational parameter of the portable electronic device and the values of the sensor of the portable electronic device, determining the at least one compensation value subject to one or more of the data representing an operational parameter of the portable electronic device, the values of the sensor of the portable electronic device, data representing an operational parameter of a remote portable electronic device with a chemical sensor, values of a sensor of the remote portable electronic device, and other data available to the remote determination unit, and transmitting the at least one compensation value via the interface to the portable electronic device.

* * * * *